United States Patent
Hanson et al.

(10) Patent No.: US 9,736,465 B2
(45) Date of Patent: Aug. 15, 2017

(54) 3D CAMERA SYSTEM

(71) Applicant: VISION RT LIMITED, London (GB)

(72) Inventors: Peter Hanson, London (GB); Gideon Hale, London (GB)

(73) Assignee: VISION RT LIMITED, London (GB)

(*) Notice: Subject to any disclaimer, the term of this patent is extended or adjusted under 35 U.S.C. 154(b) by 139 days.

(21) Appl. No.: 14/386,708

(22) PCT Filed: Apr. 25, 2013

(86) PCT No.: PCT/GB2013/051047
§ 371 (c)(1),
(2) Date: Sep. 19, 2014

(87) PCT Pub. No.: WO2013/160682
PCT Pub. Date: Oct. 31, 2013

(65) Prior Publication Data
US 2015/0062303 A1    Mar. 5, 2015

(30) Foreign Application Priority Data
Apr. 26, 2012   (GB) .................................. 1207299.7

(51) Int. Cl.
H04N 15/00    (2006.01)
H04N 13/02    (2006.01)
(Continued)

(52) U.S. Cl.
CPC ....... *H04N 13/0296* (2013.01); *A61N 5/1049* (2013.01); *H04N 5/2252* (2013.01);
(Continued)

(58) Field of Classification Search
None
See application file for complete search history.

(56) References Cited

U.S. PATENT DOCUMENTS 6,493,095 B1* 12/2002 Song .................. G01B 11/24
250/237 G
7,348,974 B2   3/2008 Smith et al.
(Continued)

FOREIGN PATENT DOCUMENTS

CN    101232572 A    7/2008
CN    102421360 A    4/2012
(Continued)

OTHER PUBLICATIONS

International Preliminary Report on Patentability and Written Opinion of the International Searching Authority for PCT/GB2013/051047.
(Continued)

*Primary Examiner* — Chikaodili E Anyikire
(74) *Attorney, Agent, or Firm* — Kenealy Vaidya LLP

(57) ABSTRACT

An exemplary embodiment of a 3D camera system for a patient positioning and monitoring system is described. In the system a pair of image detectors are provided where the image detectors are each associated with a heater thermally connected to conducting pads provided at the periphery of the image detectors. The heaters and conducting pads act to contain the image detectors in a substantially constant temperature micro climate thereby preventing external temperature variations from causing the relative positions of the image detectors to change so as to record portions of images as different pixels and hence reduce the consistency with which the identification of matching portions of images obtained by the image detectors can be utilized to determine the 3D positions of imaged objects.

22 Claims, 6 Drawing Sheets

(51) Int. Cl.
*H04N 5/225* (2006.01)
*A61N 5/10* (2006.01)
(52) U.S. Cl.
CPC ..... *H04N 13/0239* (2013.01); *H04N 13/0246* (2013.01); *A61N 2005/1059* (2013.01)

(56) References Cited

U.S. PATENT DOCUMENTS

| | | | |
|---|---|---|---|
| 7,889,906 B2 | 2/2011 | Smith et al. | |
| 2008/0011950 A1* | 1/2008 | Rose | G01T 1/1648 250/339.03 |
| 2009/0018711 A1 | 1/2009 | Ueda et al. | |
| 2009/0086020 A1 | 4/2009 | Westrick et al. | |
| 2010/0231483 A1 | 9/2010 | Bazih et al. | |
| 2011/0169918 A1 | 7/2011 | Yoo | |

FOREIGN PATENT DOCUMENTS

| | | |
|---|---|---|
| EP | 1 646 249 A1 | 4/2006 |
| GB | 2368221 A | 4/2002 |
| JP | 5-316407 A | 11/1993 |
| JP | 10-73668 A | 3/1998 |
| JP | 2007-307224 A | 11/2007 |
| JP | 4551090 B2 | 7/2010 |
| JP | 4718614 B2 | 4/2011 |
| WO | 2010/092366 A1 | 8/2010 |
| WO | 2010/105153 A2 | 9/2010 |

OTHER PUBLICATIONS

International Search Report for PCT/GB2013/051047 dated Sep. 25, 2013.
Office Action issued Dec. 1, 2015 to Chinese patent application No. 201380021922.4 (with English Translation).
Office Action issued Jan. 3, 2017 to European patent application No. 13719150.8.
Examination Report issued Jan. 19, 2017 in British Patent Office.
Office Action dated Mar. 28, 2017 in Japanese Patent Application No. 2015-507598 (with English translation).

* cited by examiner

3D CAMERA SYSTEM

This application is a national phase filing under 35 C.F.R. §371 of and claims priority to PCT Patent Application No. PCT/GB2013/051047, filed on Apr. 25, 2013, which claims the priority benefit under 35 U.S.C. §119 of British Patent Application No. 1207299.7, filed on Apr. 26, 2012, which are hereby incorporated in their entireties by reference.

The present application concerns a 3D camera system. More specifically the present application concerns a 3D camera system for monitoring the positioning and movement of patients. The invention is particularly suitable for use with radio therapy devices and computed tomography (CT) scanners and the like where detection of patient movement or irregular breathing is important for successful treatment.

Radiotherapy consists of projecting onto a predetermined region of a patient's body, a radiation beam so as to destroy or eliminate tumors existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

When a tumor is located in the thoracic or abdominal chest cavities, the position of a tumor can vary considerably (e.g. by as much as a few centimeters) throughout the breathing cycle. In order to obtain reliable CT scanning data it is therefore important to obtain data consistently at the same point within a breathing cycle.

Certain modern CT scanners are able to process CT scanning data acquired at different times within a breathing cycle to generate a representation of the 3D movement of internal organs during breathing. Such "4D" representations of organ movement are invaluable in determining a course of treatment for irradiating a cancer. Again in order for quality planning data to be generated, the timing within the breathing cycle when individual CT scans are acquired must be known so that the 4D representation accurately represents the movement of the internal organs.

When applying radiation to a patient, the gating of treatment apparatus should be matched with the breathing cycle so that radiation is focused on the location of a tumor and collateral damage to other tissues is minimized. If movement of a patient is detected the treatment should be halted to avoid irradiating areas of a patient other than a tumor location. Also if irregular breathing such as coughing is detected, treatment should be halted as such irregular breathing may cause a tumor to change location relative to the focus of a radiation beam.

For this reason a number of monitoring systems for monitoring a patient's movement and breathing during radiotherapy have therefore been proposed. These include Vision RT's patient monitoring system which has previously been described in U.S. Pat. No. 7,348,974, U.S. Pat. No. 7,889,906 and US2009-018711 all of which are hereby incorporated by reference.

In the systems described in Vision RT's patent applications, stereoscopic images of a patient are obtained and processed to generate data identifying 3D positions of a large number of points corresponding to points on the surface of an imaged patient. Such surface data can be compared with data generated on a previous occasion and used to position a patient in a consistent manner or provide a warning when a patient moves out of position.

When a patient is monitored, relatively small motions on the surface of a patient can indicate much larger motions of a tumor within a patient's thoracic or abdominal chest cavity. Improvements in the accuracy and consistency with which models of the surface of a patient can be generated are therefore desirable.

In accordance with one aspect of the present invention there is provided a stereoscopic camera system comprising: a first image detector for obtaining an image of an object from a first view point; and a second image detector for obtaining an image of an object from a second view point, fixed relative to the viewpoint of the first image detector; wherein each of the image detectors is arranged to be contained within a micro climate of substantially constant temperature.

The applicants have determined that very small changes in relative position between image detectors which arise due to external temperature variations can result in pixel drift which reduces the accuracy of a stereoscopic camera based patient monitoring system. Such changes naturally occur as the image sensors and their mountings expand and contract with variations in temperature. Although such movements are very small, they are such that the calibration of sensors can become misaligned so that portions of an image are registered in adjacent pixels. Where an image sensor is imaging a patient at a distance this very small change in location is registered as a much larger change in the position of the portion of the surface of the patient being monitored. However such errors can be substantially eliminated if steps are taken to maintain image detectors at a substantially constant temperature.

In some embodiments the arrangements for maintaining image detectors at a substantially constant temperature may comprise associating a heater with each image detector where the heater is operable to maintain the respective image detectors at a substantially constant temperature. In other embodiments a cooling device such as a peltier thermoelectric cooling device could be used to maintain a substantially constant temperature micro-climate for each sensor. The use of a heater, in however preferable as heaters enable the temperature of an image detector to be raised above the ambient air temperature and therefore avoid external variations in air temperature influencing the sensor mountings.

The image detectors may be mounted on a substrate and one or more conducting pads thermally connected to the heater associated with the image detector maybe provided around the periphery of the image detector to help maintain the detector in a substantially constant temperature micro climate.

A detector operable to detect ambient temperature may be provided so that the heaters can be arranged to cause the image detectors to be contained in a micro climate at a substantially constant temperature greater than the detected ambient temperature. Alternatively in other embodiments the heaters may be arranged to heat the image detectors to a temperature greater than the expected ambient temperature without any external detection of ambient temperature.

In some embodiments the image detectors may be mounted within a housing containing a fan wherein vents are provided in the housing and the fan is arranged to draw air into the housing via the vents and expel air out of the housing at a position remote from the image detectors. Such an arrangement largely maintains the interior of the housing at a constant temperature and thereby reduces the temperature variations which need to be compensated for by heaters or coolers adjacent the image detectors. In other embodiments circulation of air may be achieved passively through convection. In some circumstances, using passive circulation may be advantageous when this avoids drawing air of varying temperature through the camera which may occur when air is actively drawn into a housing.

In some embodiments a speckle projector will be included within the housing where the speckle projector is arranged to project a speckle pattern onto an object which can be imaged by the image detectors so that corresponding portions of images obtained by the two image detectors can be more easily matched. In such a system it is preferable that the speckle projector includes a light source which heats the interior of the housing only to a limited degree. One suitable light source could be a light emitting diode, particularly a colored light emitting diode corresponding to the desired color of speckle pattern which is to be projected onto an object. In such a system the effect of heating arising from the use of a speckle projector may be further reduced by associating the light emitting diode with a heat sink on the exterior of the housing.

In some embodiments the light source for a speckle projector may comprise a halogen lamp. Preferably the image detectors will be located remote from any such light source and any other sources of heat contained within the housing. In any embodiment but in particular in embodiments where a light source such as a halogen lamp is utilized which generates a relatively large amount of heat, a fan may be provided arranged so as to cause air drawn in via vents provided in the housing and expelled from the interior of the housing at a position remote from the image detectors having passed by the light source thereby causing heated air to be expelled from the interior of the housing.

Typically where a stereoscopic camera is to be used as part of a patient positioning system, this will be a red light emitting diode as patient's eyes are less sensitive to red light. Alternatively an infra-red light source could be used. Preferably the light source will be such to generate light of the desired waveband to avoid having to filter emitted light which can result in the reflection of light and heat back into the interior of a housing containing the image sensors.

In some embodiments the camera system may additionally comprise a processor operable to process image data received from the image detectors.

In such embodiments the processor may be operable to processes image data received from the image detectors by determining a weighted average of pixel values for a pixel and adjacent pixels. More specifically the processor is operable to process image data by applying an approximation of a Gaussian blur to blocks of adjacent pixels. By processing image data in such a way random thermal errors in image data may be substantially eliminated from the image data as the action of blurring image data causes the random errors to cancel out thereby facilitating matching between images obtained by the two image detectors.

In some embodiments the Gaussian blur applied to image data may comprise determining a weighted average by scaling a pixel value for a central pixel by a quarter, pixel values for immediately adjacent pixels by an eighth and pixel values for diagonally adjacent pixels by a sixteenth. In such an embodiment all the scaling of pixel values could be determined by performing logical shifts rather than by performing division and hence could be performed rapidly using limited processing resources.

In some embodiments the processor may be arranged to process image data received from the image detectors by scaling pixel values below a first threshold so as to increase the differences in pixel values corresponding to different light levels in darker areas of an image imaged by the image detectors. The processor may also scale pixel values above a second threshold so as to reduce the differences in pixel values corresponding to different light levels in lighter areas of an image imaged by the image detectors and map pixel values between the first and second threshold by mapping the pixel values to values between the scaled values corresponding to the first and second thresholds.

When obtaining image data of an object illuminated by a speckle pattern projected by a speckle projector, light areas generally correspond to areas well lit by the projector. However, darker areas may correspond to either darker areas in the projected pattern or areas which are substantially in shade. By scaling the image data in the way described the contrast in darker areas in an image is increased which facilitates the identification of corresponding portions of images obtained by the image detectors.

In some embodiments the scaling of image values in the manner described above can be achieved by doubling pixel values for values below a first threshold; adding a constant value to pixel values between a first and a second threshold and halving and adding a second constant value to pixel values above the second threshold. Such an embodiment would have the advantage that all the processing could be achieved through a combination of binary shifts and binary adding operations and hence could be rapidly using limited processing resources.

In some embodiments the image detectors may be arranged to generate n bit data and the processor may be arranged to reduce the bit length of the data prior to transmission from the camera system. Thus for example the image detectors may generate 10 bit data and 8 bit data may be output by the camera system or 12 bit data may be generated and 10 bit data output thereby reducing the time required to transmit image data to a computer where corresponding portions of images obtained by the image detectors can be identified so as to determine the 3D positions of surfaces corresponding to such points.

In some embodiments a reduction in data for transmission may be achieved by truncating the n bit data by not transmitting some of the least significant bits. Preferably however, rather than truncating the data, a rounding operation is performed as this improves the extent to which different patterns in image data can be identified and helps with matching corresponding points in pairs of captured images.

The stereoscopic camera system may be included as part of a patient monitoring system. In such a system a 3D position determination module may be provided which is operable to process image data output by the stereoscopic camera system to identify corresponding portions of images captured by different image detectors from different viewpoints and determine the 3D positions of points corresponding to the corresponding portions of images.

A patient monitoring system may additionally comprise a model generation module operable to generate a 3D computer wire mesh model of a surface on the basis of the 3D positions of points determined by the 3D determination module; and a matching module operable to compare a generated model with a stored model surface.

BRIEF DESCRIPTION OF THE DRAWINGS

An embodiment of the present invention will now be described with reference to the accompanying drawings in which.

SPECIFIC EMBODIMENT

Figure 1:
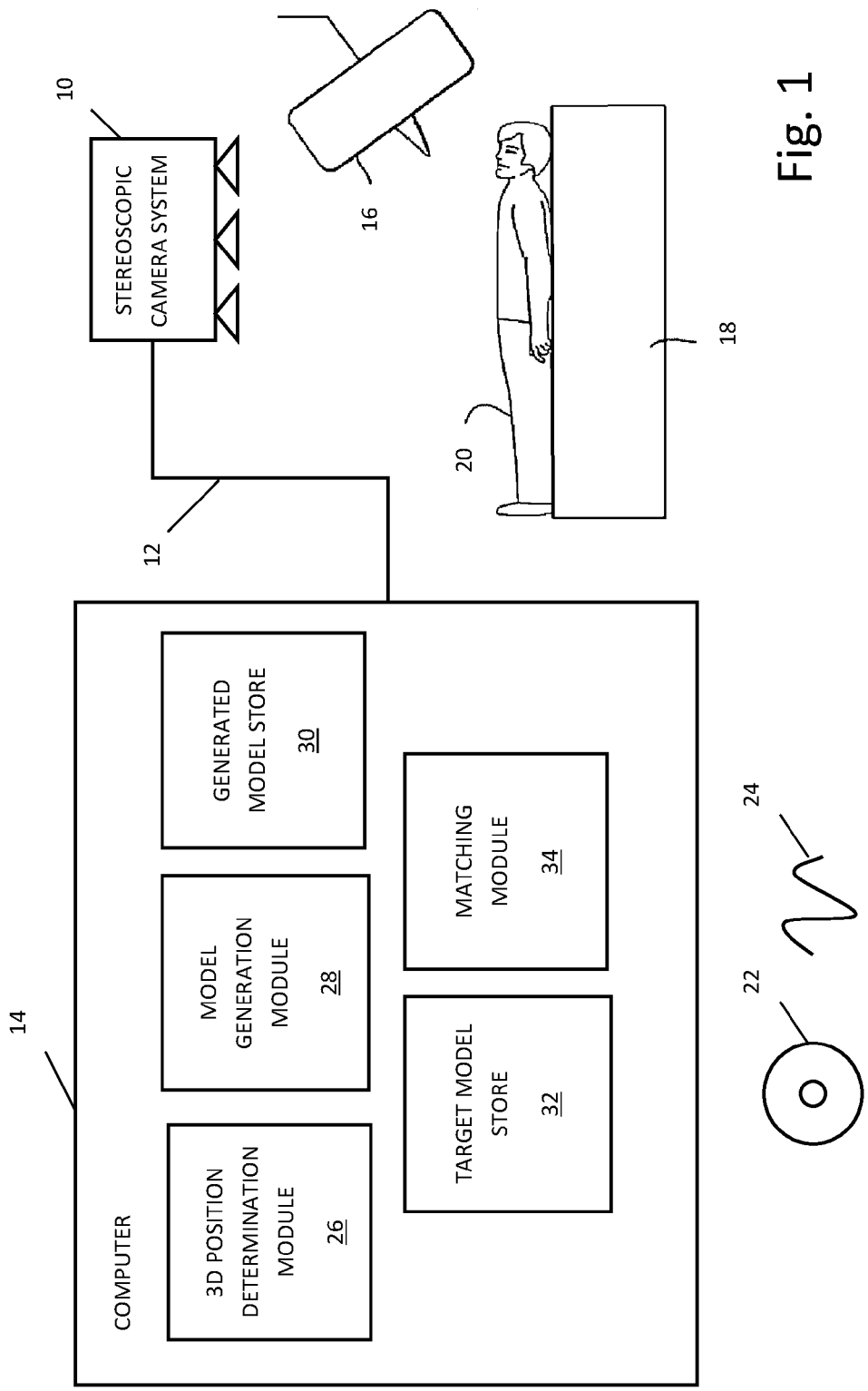
FIG. 1 is a schematic diagram of a patient monitor incorporating a stereoscopic camera system in accordance with the present invention.

FIG. 1 is a schematic diagram of a patient monitor incorporating a stereoscopic camera system 10 in accordance with an embodiment of the present invention. In this embodiment, the stereoscopic camera system 10 is connected by wiring 12 to a computer 14. The computer 14 is also connected to treatment apparatus 16 such as a linear accelerator for applying radiotherapy or an x-ray simulator for planning radiotherapy. A mechanical couch 18 is provided as part of the treatment apparatus upon which a patient 20 lies during treatment. The treatment apparatus 16 and the mechanical couch 18 are arranged such that under the control of the computer 14 the relative positions of the mechanical couch 18 and the treatment apparatus 16 may be varied, laterally, vertically, longitudinally and rotationally.

In use, the stereoscopic camera system 10 obtains video images of a patient 20 lying on the mechanical couch 18. These video images are passed via the wiring 12 to the computer 14. The computer 14 then processes the images of the patient 20 to generate a model of the surface of the patient 20. This model is compared with a model of the patient 20 generated during earlier treatment sessions. When positioning a patient 20 the difference between a current model surface and a target model surface obtained from an earlier session is identified and the positioning instructions necessary to align the surfaces determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

In order for the computer 14 to process images received from the stereoscopic camera system 10, the computer 14 is configured by software either provided on a disk 22 or by receiving an electrical signal 24 via a communications network into a number of functional modules 26-34. It will be appreciated that the functional modules 26-34 illustrated in FIG. 1 are purely notional in order to assist with the understanding of the working of the claimed invention and may not in certain embodiments directly correspond with blocks of code in the source code for the software. In other embodiments the functions performed by the illustrated functional modules 26-34 may be divided between different modules or may be performed by the re-use of the same modules for different functions.

In this embodiment, the functional modules 26-34 comprise: a 3D position determination module 26 for processing images received from the stereoscopic cameras 10, a model generation module 28 for processing data generated by the 3D position determination module 26 and converting the data into a 3D wire mesh model of an imaged computer surface; a generated model store 30 for storing a 3D wire mesh model of an imaged surface; a target model store 32 for storing a previously generated 3D wire mesh model; and a matching module 34 for determining rotations and translations required to match a generated model with a target model.

In use, as images are obtained by the stereoscopic camera system 10, these images are processed by the 3D position determination module 26 to identify 3D positions of corresponding points in pairs of images. This is achieved by the 3D position determination module 26 identifying of corresponding points in pairs of images obtained by the stereoscopic camera system 10 and then determining 3D positions for those points based on the relative positions of corresponding points in obtained pairs of images and stored data identifying the relative positions of cameras obtaining the images.

Typically the identification of corresponding points is based on analysis of image patches of around 16×16 pixels. In order to assist with identifying and matching corresponding patches as will be described the stereoscopic camera system 10 is arranged to project a random or quasi random speckle pattern onto the patient 20 being imaged so that different portions of the surface of the patient 20 can be more easily distinguished. The size of the speckle pattern is selected so that different patterns will be apparent in different image patches.

The position data generated by the 3D position determination module 26 is then passed to the model generation module 28 which processes the position data to generate a 3D wire mesh model of the surface of a patient 20 imaged by the stereoscopic cameras 10. In this embodiment the 3D model comprises a triangulated wire mesh model where the vertices of the model correspond to the 3D positions determined by the 3D position determination module 26. When such a model has been determined it is stored in the generated model store 30.

When a wire mesh model of the surface of a patient 20 has been stored, the matching module 34 is then invoked to determine a matching translation and rotation between the generated model based on the current images being obtained by the stereoscopic cameras 10 and a previously generated model surface of the patient stored in the target model store 32.

The determined translation and rotation can then be sent as instructions to the mechanical couch 18 to cause the couch to position the patient 20 in the same position relative to the treatment apparatus 16 as they were when they were previously treated. Subsequently, the stereoscopic cameras 10 can continue to monitor the patient 20 and any variation in position can be identified by generating further model surfaces and comparing those generated surfaces with the target model stored in the target model store 32. If it is determined that a patient has moved out of position, the treatment apparatus 16 can be halted and the patient 20 repositioned, thereby avoiding irradiating the wrong parts of the patient 20.

As irradiation of adjacent tissues can be harmful, it is very important that image data is captured in a manner which maximizes the consistency of image data obtained at different times. The applicants have proposed a number of developments which increase data consistency and hence improve patient monitoring.

Figure 2:
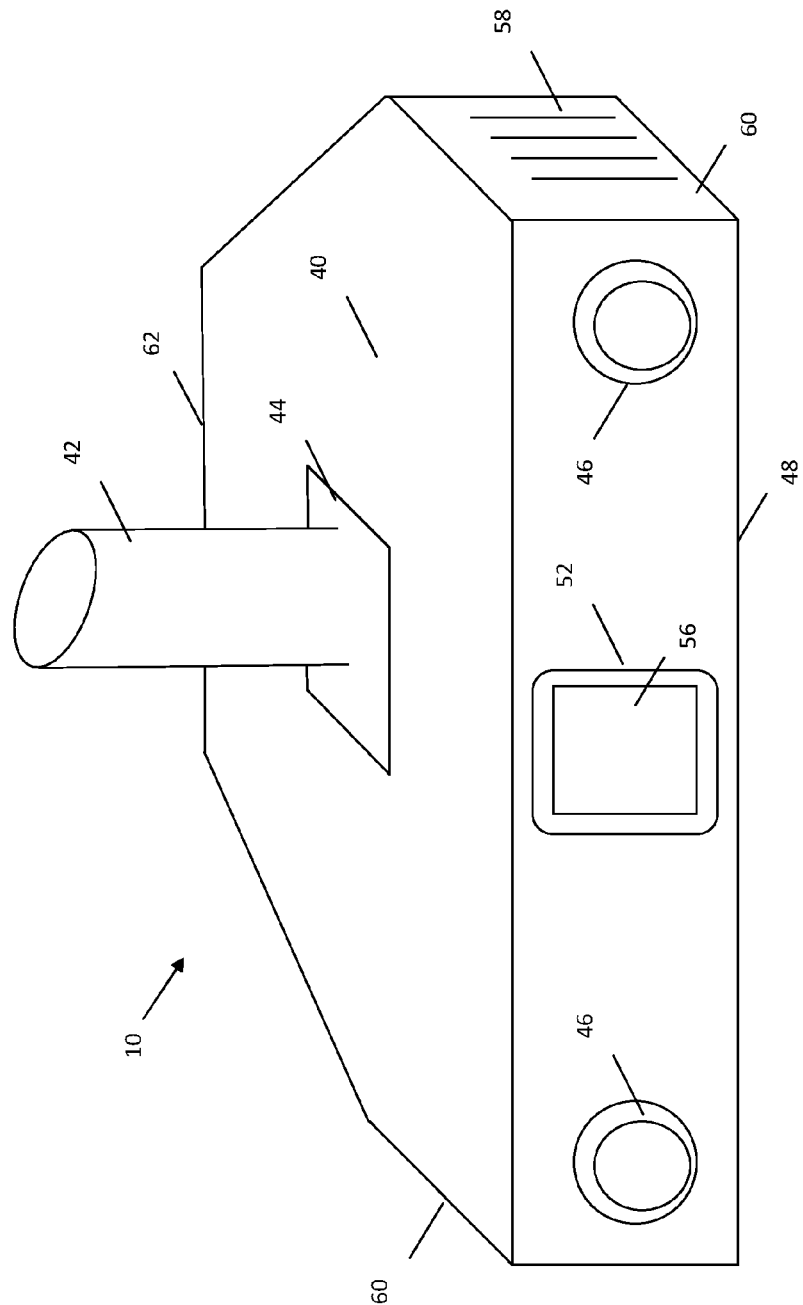
FIG. 2 is a schematic perspective view of the exterior of the camera system of FIG. 1.
Figure 3:
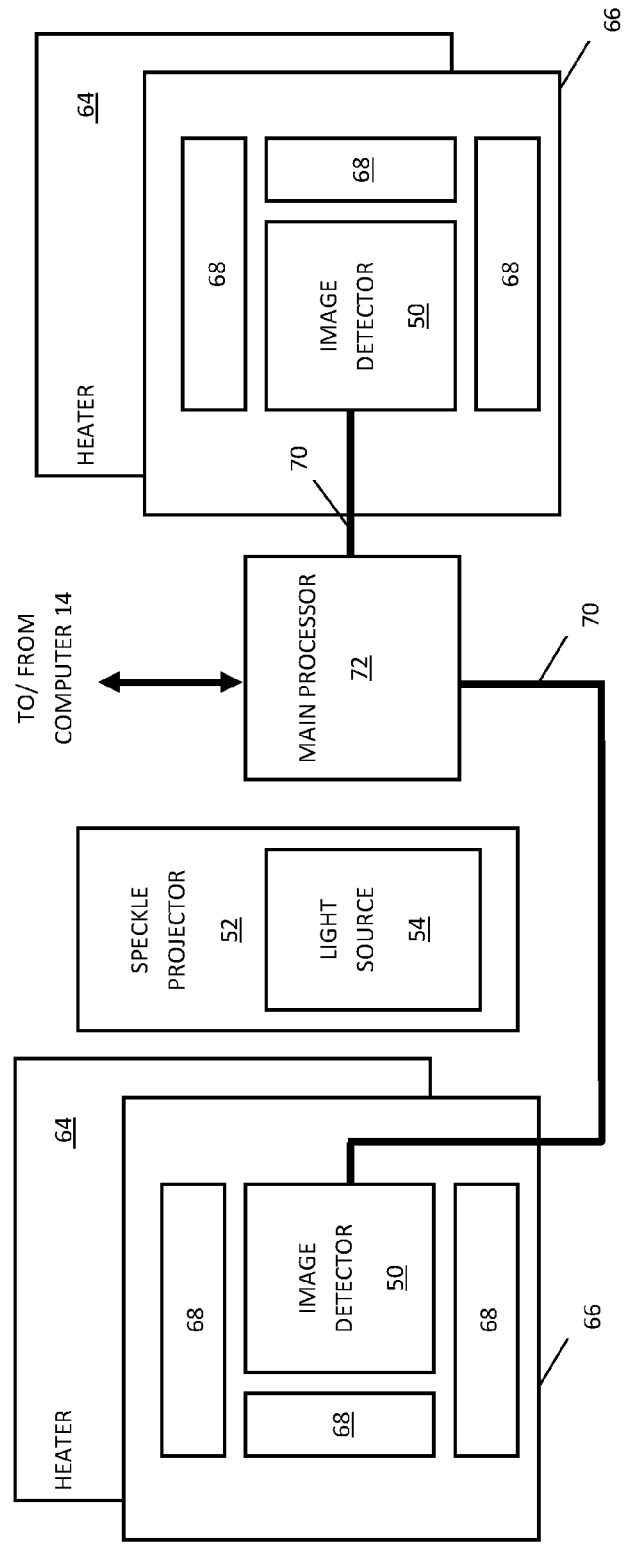
FIG. 3 is a schematic block diagram of the interior of the stereoscopic camera system of FIG. 1.

FIG. 2 is a schematic perspective view of the exterior of the camera system 10 and FIG. 3 is a schematic block diagram of the interior of the stereoscopic camera system 10 in accordance with an embodiment of the present invention.

In this embodiment the camera system 10 comprises a housing 40 which is connected to a bracket 42 via a hinge 44. The bracket 42 enables the camera system 10 to be attached in a fixed location to the ceiling of a treatment room whilst the hinge 44 permits the orientation of the camera system 10 to be orientated relative to the bracket 42 so that the camera system 10 is arranged to view a patient 20 on a mechanical couch 18.

A pair of lenses 46 are mounted at either end of the front surface 48 of the housing 40. These lenses 46 are positioned in front of image detectors 50 contained within the housing 40. In this embodiment the image detectors 50 comprise CMOS active pixel sensors. In other embodiments charge coupled devices could be used. The image detectors 50 are arranged behind the lenses 46 so as to capture images of a patient 20 via the lenses 46.

A speckle projector 52 is provided in the middle of the front surface 48 of the housing 40 between the two lenses 46. The speckle projector 52 includes a light source 54 which in this embodiment comprises a 12W red LED light. In other embodiments other light sources such as a halogen lamp could be used.

The speckle projector 52 is arranged to illuminate a patient 20 with a non-repeating speckled pattern of infrared light so that when images of a patient 20 are captured by the two image detectors corresponding portions of captured images can be distinguished. To that end light from the light source 54 is directed via a film 56 with a random speckle pattern printed on the film. As a result a pattern consisting of light and dark areas is projected onto the surface of a patient 20.

A series of vents 58 are provided in the side walls 60 of the housing 40. Further vents (not shown) are provided in the rear 62 of the housing 40. A fan (not shown) connected to a temperature sensor (also not shown) is contained within the housing 40. The temperature sensor is arranged to monitor the ambient temperature within the interior of the housing 40 and if this varies to activate the fan to draw air in via the vents 58 in the side walls 60 of the housing 40 and expel the air via the vents at the rear 62 of the housing 40. In this way an air flow of air at room temperature is caused to circulate within the housing 40 and maintain the interior of the housing 40 at a substantially constant temperature.

To minimize temperature variations within the housing 40, immediately adjacent the image detectors, the vents 58 are provided in the side walls of the housing 40 slightly removed from the sensors 50 so that when air is drawn into the interior of the housing 40, it is not drawn past the sensors 50. Rather the fan and temperature sensor are utilized to maintain the temperature of the main body of air within the interior of the housing 40 at a substantially constant level with the air adjacent the sensors 50 being kept at a constant temperature through passive communication and convection with this main body of air. By separating the vents 58 from the sensors 50, the activation and deactivation of the fan does not cause sudden changes in temperature adjacent the sensors 50.

The applicants have appreciated that sensitivity to temperature is unexpectedly a significant cause of loss of accuracy in a stereoscopic camera based patient monitoring system. Variations in temperature cause small variations in the position of the image detectors 50. Due to the sensitivity of the image detectors such changes do not have to be high in order for one part of an image corresponding to a pixel to be registered at a different pixel. Thus for example it has been determined that movements as small as 2.5 micrometers may cause one part of an image to be registered in an adjacent pixel. When this occurs the accuracy with which 3D positions of points imaged by the image detectors 50 declines.

To substantially eliminate this source of error, in this embodiment a heater 64 is provided attached to the rear of the circuit board 66 on which each of the image detectors 50 is mounted. Additionally on the circuit board a series of copper conducting pads 68 are provided surrounding the image detector 50 except on one side enabling wiring 70 to connect the image detectors 50 to a main processor 72. When the heaters 64 are arranged to heat to a temperature above ambient room temperature the effect of the heaters 64 and the conducting pads 68 is to substantially isolate the image detectors 50 from external variations in temperature. Thus effectively the image detectors 50 are enclosed in their own constant temperature micro-climates.

This is particularly the case where as far as possible the image detectors 50 are removed from other external heat sources. In the described embodiment this is achieved by for example using a red LED as a light source 54 for the speckle protector 52 thus reducing internal heating which occurs when for example an iridescent light bulb is used as less power is required to generate the required light levels and further as the generated light is only generated in a relatively narrow wave band it is not necessary to include a colored film to remove light at other wave bands which acts to reflect light and heat back within the body of the housing 40.

In addition the arrangement of the vents 58 adjacent the image detectors 50 and the direction of airflow away from the detectors 50 and out through the rear 62 of the housing 40 also adds to the extent to which the image detectors 50 can be maintained at a constant temperature as a constant stream of air at ambient temperature passes by the detectors 50 and heating arising from the workings of the camera system 10 is ejected from the rear 62 of the housing 40. The detectors 50 are thereby largely shielded from outside heat sources and remain at a constant temperature as determined by the heaters 64.

Figure 4:
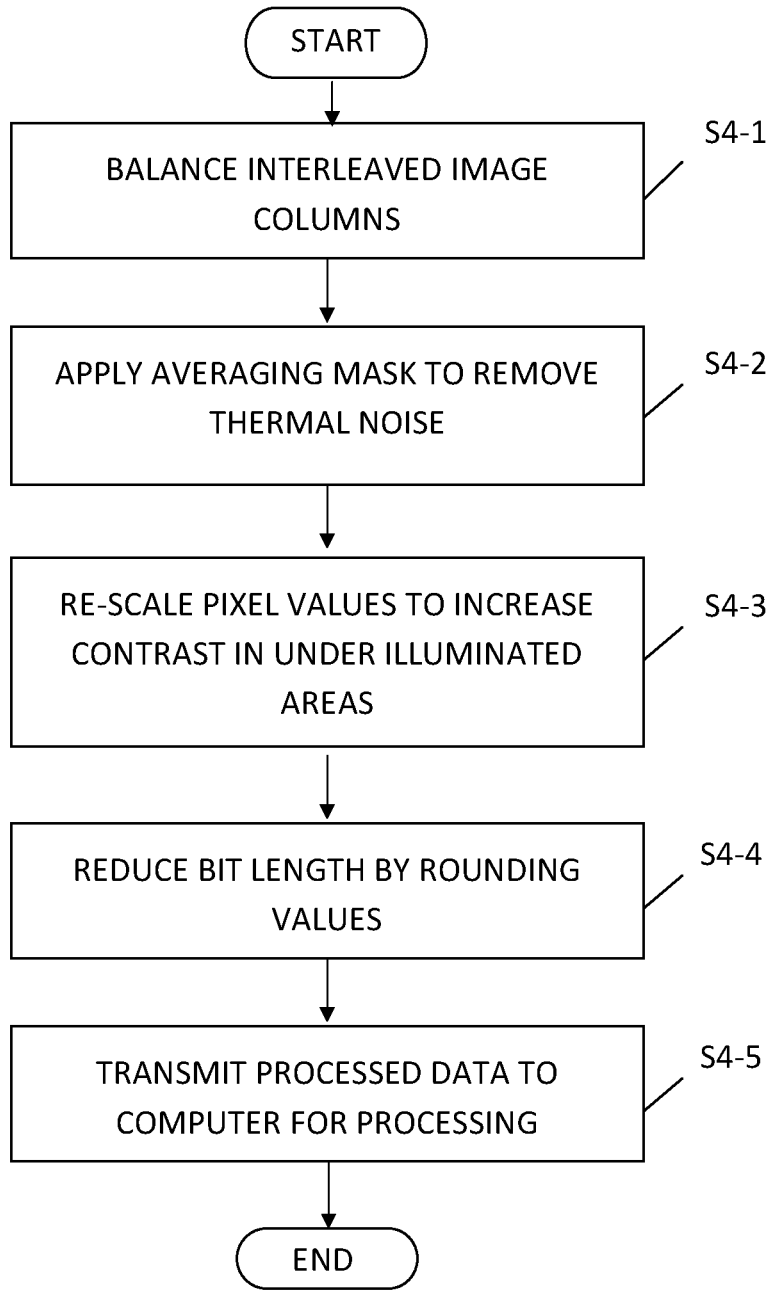
FIG. 4 is a flow diagram of the processing undertaken by the main processor of the stereoscopic camera system of FIG. 1.

The processing of image data by the image detectors 50 to the main processor 72 will now be described with reference to the flow diagram of FIG. 4.

Image data obtained by an image detector such as a CMOS active pixel sensor will comprise a matrix of pixel values indicating the relative brightness or darkness of a portion of an image. Typically such pixel values will be 10 bit pixel data with values ranging from 0 to 1023 where 0 indicates a pixel in an image being completely dark and 1023 indicates a pixel being bright white.

When such image data is received by the main processor 72, as an initial step (s4-1) the processor modifies the image data associated with alternate columns in the matrix by applying a correction factor to those lines.

Where a CMOS active pixel sensor is used as an image detector, frequently alternate columns in an image will be updated separately so as to enhance readout performance. Where such data is captured and updated separately this can lead to artifacts appearing in an image where the average brightness of alternate columns differs. Such artifacts can be removed by determining the average brightness of the sets of columns corresponding to columns updated independently. Correction factors for causing the average brightness of each set to be equal can then be determined and the pixel values for columns in an image updated by adding the determined correction values to the values output by the image detector 50.

Having corrected the image data to account for artifacts arising from the independent updating of interleaved columns in an image, the main processor then (s4-2) processes the image data to remove thermal noise from the image.

More specifically, errors in image values arise randomly due to thermal effects, slightly increasing or decreasing the values obtained from an image detector 50. This can lead to difficulties in identifying corresponding portions of images captured by the two image detectors 50.

To remove such errors, in this embodiment the main processor 72 takes advantage of the fact that such errors arise randomly and therefore the numbers of errors which result in increases in pixel values should be equal to the numbers of errors which result in lower pixel values.

This is achieved by determining a scaled average of groups of pixels using a mask which approximates a Gaussian blur. A suitable mask is illustrated in FIG. 5.

Figures 5, 6:
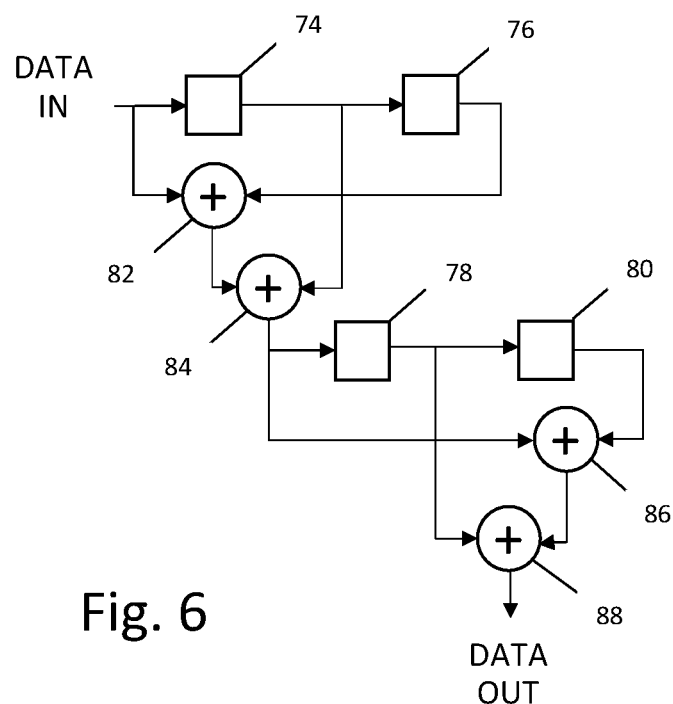
FIG. 5 is an illustration of an averaging mask for processing an image to remove the effects of thermal noise.
FIG. 6 is a schematic block diagram of a filter for implementing the averaging mask of FIG. 5.

In the case of FIG. 5 a pixel value for a pixel at position x,y would be determined by calculating the sum of ¼ the pixel value of the pixel at x,y plus ⅛ of the sum of the pixel values for the pixels at positions (x−1,y), (x+1,y), (x,y−1) and (x,y+1) plus ¹⁄₁₆ of the sum of the pixel values for the pixels at positions (x−1, y−1), (x−1,y+1), (x+1, y−1) and (x+1, y+1).

Where each of the pixels is associated with a random error $\epsilon$, the effect of the summing the errors across the 9 adjacent pixels will be to cancel out the error in the original pixel at the expense of a slight loss in the acuity of the image data. However, where similar processing is undertaken on image data received from both image detectors 50, this loss of acuity will be the same across the images and hence unlike the original random thermal errors will not affect the ease with which corresponding portions of images can be identified.

The small loss in image acuity does not adversely affect the processing of a matching algorithm where any patch matching algorithm matches larger groups of pixels than are processed by the smoothing algorithm. Thus for example in the present embodiment the smoothing algorithm is arranged to process 3×3 blocks of pixels. Such processing would not adversely affect a patch matching algorithm which for example undertook matching of 16×16 pixel image patches.

It will be appreciated that when determining the scaled sum described above, pixel values for the images with random thermal errors removed can be determined solely by performing suitable binary adding and shifting operations and hence an image can be processed to remove such errors very rapidly. More specifically division by 4, 8 or 16 can be determined by performing a binary shift 2, 3, or 4 times. The described scaled averaging can therefore be performed rapidly using very limited processing resources and hence would not impose significant delays before the processed image data can be transmitted to the computer 14 for processing to match corresponding points in the captured images.

A suitable circuit for implementing the averaging filter of FIG. 5 is shown in FIG. 6. In this example the circuit comprises two latches 74, 76, two line stores 78,80 and a set of four binary adders 82-88. The latches 74,76 are arranged to store pixel value data until they are informed that the next pixel in an image is to be read out. In contrast the pair of line stores 78,80 are arranged to store data for a lines of image data and then pass the data onto the next latch as well as output individual items of data to the binary adders 86, 88 one by one. Each of the binary adders 82-88 is arranged to receive a pair of inputs and output a sum of the inputs with a shifted result so that the output value is one half of the sum of the pair of inputs.

When data is received initially it is read into a first latch 74. Subsequently when the next item of pixel data is received, data previously in the first latch 74 released and passed to the second latch 76 and the new data is written into the first latch 74. The effect of the first two latches 74,76 is therefore to provide values corresponding to the pixel values for three adjacent pixels to the first two binary adders 82,84. When this data is made available, one of the binary adders 82 sums the first and third pixel values and output a value corresponding to half that sum to the second binary adder 84. The second binary adder 84 adds this value to the value of the second pixel in the set of pixels being processed and outputs half that sum.

Thus for example if the pixel values $A_1$, $A_2$ and $A_3$ where to be received, the output from the first binary adder 82 would be $(A_1+A_3)/2$ and the output from the second binary adder 84 would be $(A_1+A_3)/4+A_2/2$.

This value is passed to a first one of the line stores 78 and also to the third binary adder 86. As noted above the two line stores 78,80 are arranged store data for a line of image data. The first line store 78 is arranged to pass data for a line of an image being processed to the second line store 80 in response to a signal indicating that the next line of image data is being read out. Additionally the line stores 78,80 are arranged to output individual items of data one by one to the third and fourth adders 86,88 each time a new item of data is received into the latch. The effect of this is that the line stores 78,80 output items of data and binary adders 86,88 process the data calculated for a line of three adjacent pixels in a similar manner to the processing of individual items of pixel data by the first and second latches 74,76 and adders 82,84 except that the data is delayed by one or two lines.

Thus in the case of processing a portion of an image with pixel values $A_1$, $A_2$, $A_3$, in a first line $B_1$, $B_2$, $B_3$, in a second line and $C_1$, $C_2$ and $C_3$ in the third line the output from the third 86 binary adder will be $(A_1+A_3)/8+A_2/4+(C_1+C_3)/8+C_2/4$ which is passed on to the fourth binary adder 88. When the fourth binary adder receives this data this will then be combined with the result of processing the second line of the image output by the second binary adder 84 and stored in the first line store 78 which will be $(B_1+B_3)/4+B_2/2$ with the result that the final value output will be $A_1+A_3)/16+A_2/8+(B_1+B_3)/8+B_2/4+C_1+C_3)/16+C_2/8$ i.e. the required scaled sum of the 3 by 3 block of pixels.

Having processed the captured image data to reduce the effects of thermal noise, the main processor then proceeds to re-scale (s4-3) image data for pixels in the image to increase contrast in under illuminated areas.

As noted above, in order so that the 3D position determination module 26 can identify corresponding points in images obtained by the two image detectors 50, a speckle projector 52 projects a non-repeating (e.g. random or quasi random) speckle pattern onto the surface of a patient 20. Where a patient 20 is directly illuminated by the speckle projector 52, this will cause the surface of the patient to appear as either bright areas—corresponding to areas of illumination or dark areas corresponding to dark areas in the projected speckle pattern and it is easy to distinguish between the two. However, in parts of the surface of a patient which are not so well illuminated (e.g. areas in shadow), the differences in appearance between illuminated areas and areas corresponding to darker points in the projected speckle pattern will not be as great.

Thus in order to increase the extent to which corresponding points in obtained images can be matched, in this embodiment the pixel values obtained after removing thermal noise are scaled in the following way:

1) All pixel values less than 128 are doubled by performing a logical shift left.

Thus for example binary pixel value 12: 0000001100 would be processed to become binary pixel value 24: 000011000

2) All pixel values between 128 and 768 are increased by adding 128 to the original pixel value;

Thus for example binary pixel value 296: 0100101000 would be processed to become binary pixel value 424: 0110101000

3) All pixel values between 768 and 1024 are halved by performing a logical shift right and 512 is added to the result.

Thus for example binary pixel value 998: 1111100110 would be processed to become binary pixel value 1011: 111111001

Figure 7:
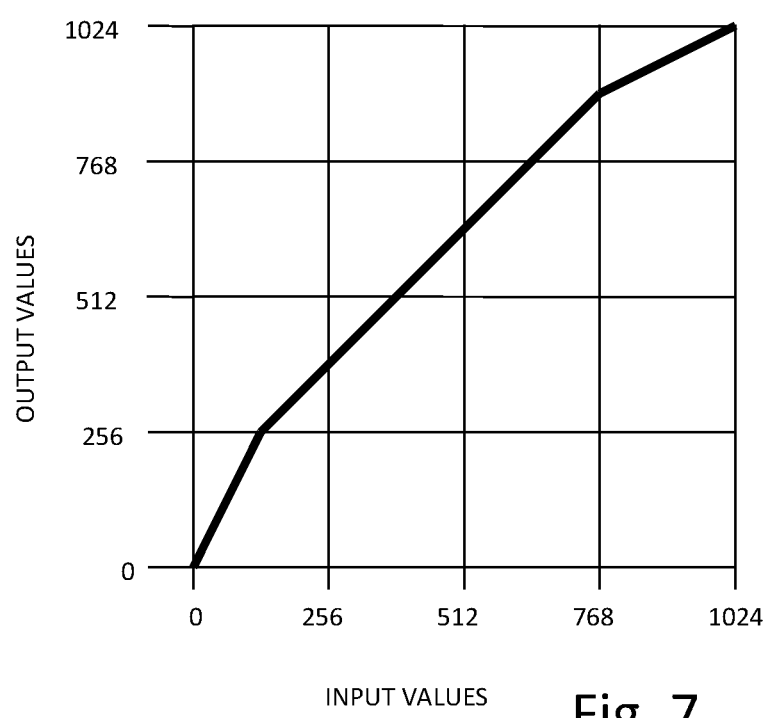
FIG. 7 is a graph illustrating relationships between scaled input and output values increasing contrast in under illuminated areas.

FIG. 7 is a graph illustrating the relationships between scaled input and output values processed in the manner described above.

As will be apparent the effect of the processing is to map the original input values so that differences between pixels having values less than 128 are increased and the differences between pixel having values over 768 are reduced.

It is desirable that as many points corresponding to points on the surface of a patient can be identified. The applicants have appreciated that where a portion of a patient 20 is well illuminated it is still possible to distinguish between light and dark areas of projected speckle pattern even when the contrast in such areas is reduced. This contrasts with less well illuminated areas where the differences between the light and dark areas of projected speckle may be small. Thus the above processing has the effect of increasing the numbers of corresponding points in obtained pairs of images that the 3D position determination module 26 may match.

Having scaled the pixel values (s4-3) the main processor 72 then proceeds to reduce the volume of data to be transmitted to the computer 14 by rounding (s4-4) the pixel values thereby converting the 10 bit data to 8 bit data for faster data transmission.

One option to achieve such a reduction in data size would be to truncate the 10 bit data by ignoring the two least significant bits. Although this would achieve the desired data reduction, this would involve abandoning any information contained in the least significant bits. Thus for this reason rather than performing a truncation operation, a rounding operation is preferable as this enables any information retained in the least significant bits to be utilized and thereby improve the accuracy of the point matching. Having performed the rounding operation, the main processor 72 then (s4-5) proceeds to transmit the processed data to the computer 14 via the wiring 12 where the 3D position determination module 26 processes the received image data to identify corresponding portions of the images captured by the two image detectors 50 and utilizes the correspondences and information about the relative positioning of the image detectors 50 to determine the 3D position of points on the surface of an imaged patient 20. When processed image data has been transmitted to the computer 14, the main processor 72 then proceeds to obtain the next frame of image data from the two image detectors 50 for processing. Thus in this way the computer 14 is able to monitor the movement and location of the patient 20 in real time.

FURTHER EMBODIMENTS AND MODIFICATIONS

Although in the above described embodiment a camera system including speckle projector 52 including an LED light source has been described, it will be appreciated that an alternative light sources such as a halogen lamp might be used. It will also be appreciated that although in the above embodiment a system has been described where a temperature sensor and a fan are included within the body of the system in some embodiments the sensor and fan could be omitted.

It will also be appreciated that as an alternative or in addition to using the circulation of air to reduce the buildup of heat within the interior of a housing 40, in some embodiments heat sources such as an LED light source 54 or the processor 72 could be associated with one or more heat sinks provided on the exterior of the housing 40 so that the heating within the interior of the housing 40 caused by the light source 54 or processor 72 is substantially eliminated.

Although in the above embodiment image data has been described as being processed to reduce the effects of thermal noise, in some embodiments it may be preferable to process only parts of an image in the manner described. In particular it may be preferable to process only those parts of an image corresponding to areas of low illumination. This is because where an image is well illuminated relative size of the thermal errors will be much less significant.

In such an embodiment a modified filter system such as that illustrated in FIG. 6 could be utilized. More specifically, the illustrated system could be modified to cause unprocessed data from the first latch 74 to be stored in a further line store and released so as to provide an unfiltered version of the image data which is synchronized with the output of the fourth binary adder 88. The system could then choose between the processed and unprocessed data depending upon the perceived level of illumination in an area of an image.

Although in the above embodiment, image processing has been described as taking place within the stereoscopic camera system 10 and the computer 14, it will be appreciated that the described processing could take place entirely in one location or the other or could be divided between the stereoscopic camera system 10 and the computer 14.

It will also be appreciated that although processing within the stereoscopic camera system has been described as taking place by means of being processed by a main processor 72, the processing could be undertaken either by processing undertaken by a programmable array or alternatively could be undertaken by suitable software.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier could be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A stereoscopic camera for monitoring the position and movement of patients, comprising:
    a first image detector for obtaining an image of a patient from a first view point a distance away from the patient being monitored;
    a second image detector for obtaining an image of the patient from a second view point;
    mountings substantially fixing the positions and viewpoints of the first image detector and the second image detector relative to each other; and
    a micro climate system that includes at least one conducting pad and a heater that are configured to heat to a temperature above ambient room temperature to substantially isolate each of the image detectors from external variations in temperature, thereby reducing variations in the relative positions and viewpoints of the first image detector and the second image detector due to thermal contraction and expansion of the mountings.

2. The stereoscopic camera system of claim 1, wherein each of the image detectors is arranged to be contained within a micro climate of substantially constant temperature by being associated with a heater or cooler operable to maintain the image detector at a substantially constant temperature.

3. The stereoscopic camera system of claim 1, where each of the image detectors is mounted on a substrate.

4. The stereoscopic camera system of claim 2, further comprising a detector operable to detect ambient temperature wherein the heaters are arranged to cause the image detectors to be contained in a micro climate at a substantially constant temperature greater than the detected ambient temperature.

5. The stereoscopic camera system of claim 1, further comprising a speckle projector arranged to project a speckle pattern onto an object visible from the first and second viewpoints.

6. The stereoscopic camera system of claim 5, wherein the speckle projector comprises a halogen lamp and the speckle projector and the image detectors are mounted within a housing together with a fan wherein vents are provided in the housing with the fan being arranged to cause air to be drawn in via the vents and expelled at a position remote from the image detectors passing the halogen lamp.

7. The stereoscopic camera system of claim 5, wherein speckle projector comprises a light emitting diode and the speckle projector and the image detectors are mounted within a housing wherein the light emitting diode is associated with a heat sink on the exterior of the housing.

8. The stereoscopic camera system of claim 1, further comprising a processor operable to process image data received from the image detectors.

9. The stereoscopic camera system of claim 8, wherein the processor is operable to process image data received from the image detectors by determining a weighted average of pixel values for a pixel and adjacent pixels.

10. The stereoscopic camera system of claim 9, wherein the processor is operable to process image data by applying an approximation of a Gaussian blur to blocks of adjacent pixels.

11. The stereoscopic camera system of claim 10, wherein the weighted average comprises scaling a pixel value for a central pixel by a quarter, pixel values for immediately adjacent pixels by an eighth and pixel values for diagonally adjacent pixels by a sixteenth.

12. The stereoscopic camera system of claim 8, wherein the processor is operable to process image data received from the image detectors by scaling pixel values below a first threshold so as to increase the differences in pixel values corresponding to different light levels in darker areas of an image imaged by the image detectors.

13. The stereoscopic camera system of claim 12, wherein the processor is operable to process image data received from the image detectors by scaling pixel values above a second threshold so as to reduce the differences in pixel values corresponding to different light levels in lighter areas of an image imaged by the image detectors.

14. The stereoscopic camera system of claim 13, wherein the processor is operable to process image data received from the image detectors associated with pixel values between the first and second threshold by mapping the pixel values to values between the scaled values corresponding to the first and second thresholds.

15. The stereoscopic camera system of claim 8, wherein the processor is operable to reduce the bit length of image data prior to transmission from the camera system by truncating the pixel values by eliminating the least significant bits of image data.

16. The stereoscopic camera system of claim 8, wherein the processor is operable to reduce the bit length of image data prior to transmission from the camera system by utilizing the least significant bits of image data to determine a rounding of the more significant bits of image data for pixels in the image.

17. A patient monitoring system for monitoring the position and movements of patients, comprising:
    a first image detector for obtaining an image of a patient from a first view point a distance away from the patient being monitored;
    a second image detector for obtaining an image of the patient from a second view point;
    mountings substantially fixing the positions and viewpoints of the first image detector and the second image detector relative to each other;
    a micro climate system that includes at least one conducting pad and a heater that are configured to heat to a temperature above ambient room temperature to substantially isolate each of the image detectors from external variations in temperature, thereby reducing variations in the relative positions and viewpoints of the first image detector and the second image detector due to thermal contraction and expansion of the mountings; and
    a 3D position determination module operable to process image data output by the stereoscopic camera system to identify corresponding portions of images captured by different image detectors from different viewpoints and determine the 3D positions of points corresponding to the corresponding portions of images.

18. The patient monitoring system in accordance with claim 17, further comprising:

a model generation module operable to generate a 3D computer wire mesh model of a surface on the basis of the 3D positions of points determined by the 3D determination module; and a matching module operable to compare a generated model with a stored model surface.

19. The stereoscopic camera system of claim 1, wherein the at least one conducting pad is provided around a periphery of each of the image detectors.

20. The stereoscopic camera system of claim 19, wherein multiple conducting pads surround each of the image detectors on multiple sides thereof.

21. The stereoscopic camera system of claim 20, wherein the multiple conducting pads surround each of the image detectors except on one side thereof.

22. The stereoscopic camera system of claim 1, wherein the at least one conducting pad is copper.

* * * * *